United States Patent [19]

Macaro et al.

[11] Patent Number: 4,918,003
[45] Date of Patent: Apr. 17, 1990

[54] BIOLOGICAL TEST DEVICE FOR STEAM STERILIZERS

[75] Inventors: Louise Macaro, Mt. Vernon; John Dyckman, Monroe, both of N.Y.; Thomas A. Augurt, Stamford, Conn.; Andrew Zwarun, Roslyn Heights, N.Y.

[73] Assignee: Propper Manufacturing Company, Inc., Long Island City, N.Y.

[21] Appl. No.: 251,976

[22] Filed: Sep. 29, 1988

Related U.S. Application Data

[63] Continuation of Ser. No. 771,810, Aug. 30, 1985, abandoned.

[51] Int. Cl.[4] .............................................. C12M 1/34
[52] U.S. Cl. ...................................... 435/31; 116/206; 116/207; 116/216; 206/305; 422/58; 435/299; 435/805; 436/1
[58] Field of Search .................... 435/31, 805, 299; 436/1; 422/56-58; 116/206, 207, 216; 206/569, 305, 439

[56] References Cited

U.S. PATENT DOCUMENTS

| | | | |
|---|---|---|---|
| 3,420,363 | 1/1969 | Blickensderfer | 53/472 |
| 4,136,141 | 1/1979 | Bauer et al. | 53/472 |
| 4,240,240 | 12/1980 | Cohen | 53/472 |
| 4,293,070 | 10/1981 | Ohlbach | 53/472 |
| 4,486,387 | 12/1984 | Augurt | 422/58 |
| 4,579,715 | 4/1986 | Bruso | 422/58 |
| 4,596,696 | 6/1986 | Scoville, Jr. | 206/439 |
| 4,636,472 | 1/1987 | Bruso | 435/31 X |

OTHER PUBLICATIONS

"Guide to Good Hospital Practice: Steam Sterilization & Sterility Assurance; AAWI Recommended Practice", Series Sections 7.5.1–7.6.2.

*Primary Examiner*—Barry S. Richman
*Assistant Examiner*—Jill Johnston
*Attorney, Agent, or Firm*—Amster, Rothstein & Ebenstein

[57] ABSTRACT

A disposable package is adapted to simulate the steam permeability and other qualities of the linen pack previously used to test the functioning of a steam sterilizer using a biological test device. The biological test device comprises spores on an appropriate carrier, either in a self-contained biological device or as a spore strip. The biological test device is placed within applicant's specially constructed package and the package is placed within the sterilizer, which is then cycled through a conventional sterilization cycle. During the sterilization cycle, applicant's package simulates the standard sterilizer linen pack previously used for such tests. After the sterilization cycle, sterility of the spore preparation is evaluated by incubating the spores in a culture medium to determine whether the spore population has been adequately destroyed.

11 Claims, 1 Drawing Sheet

BIOLOGICAL TEST DEVICE FOR STEAM STERILIZERS

This is a continuation of co-pending application Ser. No. 771,810 filed on Aug. 30, 1985 now abandoned.

The present invention relates generally to the sterilization of medical and surgical products and more specifically to a disposable test package adapted to contain a biological test device and to be used in a steam sterilizer to evaluate the proper performance of the sterilizer.

Medical dressings and instruments are conventionally sterilized by steam in an autoclave. The materials to be sterilized are assembled into functional packs containing different materials which may be needed in an anticipated procedure, and several such packs are placed in the autoclave. Air is then eliminated from the autoclave chamber and replaced by steam at desired temperatures and for determined times which have been found to properly sterilize the autoclave contents. In one type of autoclave, steam replaces air by normal gravity displacement, with the steam being introduced into the chamber and driving the air out. In a newer type of sterilizer, the air in the chamber is first evacuated by a vacuum system before steam is introduced. Both types of systems, referred to respectively as gravity displacement and prevacuum systems, continue to be used today.

In order to assure the proper functioning of the autoclave, good practice requires that the autoclave be periodically tested to insure that the contents of the sterilizer are undergoing a proper sterilization cycle. Faults in the sterilizer equipment such as, inadequate temperature, inadequate time, or other defects may result in nonsterile products since the critical parameters for sterilization have not been attained. Since instruments or dressings being sterilized are conventionally assembled into packs and placed in the sterilizer, the normal cycle times or the cycling of vacuum and steam are designed to remove air from the pack so as to provide proper penetration of steam into the pack at adequate temperature and time to sterilize the pack contents. Improper sterilization of any portion of the pack may contaminate a surgical procedure and cause serious complications.

U.S. Pat. No. 4,486,387 issued Dec. 4, 1984 in the name of Thomas Augurt describes a disposable prevacuum steam sterilizer test device which is adapted to be positioned in the sterilizer as the sterilizer is processed through a sterilization cycle to identify faults in the sterilizer which would have a tendancy to trap air in normal towel packs. The test device described in the Augurt patent is designed to replicate the pack used in the testing procedure described by J. H. Bowie, et al. in the Lancet, Mar. 16, 1963 at pages 586-587, which procedure has become a standard test protocol for steam autoclaves. In addition to this test protocol, which normally uses sheets of test material having special inks adapted to change color in response to adequate sterilization conditions, good procedures also require the periodic testing of the sterilizer using a biological test device and a different pack construction. Whereas the Bowie and Dick protocol (described in the Augurt patent and replicated by the Augurt device) functions with chemically treated test sheets, the biological test procedure employs live spores on an appropriate carrier positioned within a specially designed pack in a full sterilizer.

This conventional procedure is described in "Guide to Good Hospital Practice: Steam Sterilization and Sterility Assurance" issued by the Association for the Advancement of Medical Instrumenation (AAMI) as part of AAMI's "Recommended Practice" series. According to the AAMI, a biological indicator should be used no less than weekly for each sterilizer and preferably should be used for each load. The biological indicator test pack is described in Section 7.6.2 of the AAMI Recommended Practice and consists of muslin surgical gowns, towels, gauze sponges, lap sponges and other materials of a recommended size and weight. In this test, a spore strip or other spore containing test device is placed in the center of a pack which has maximum dimensions of twelve inches by twelve inches by twenty inches in size and weighs approximately 10 to 12 pounds. The pack is placed in a normally loaded sterilizer for processing.

As in the case of the Bowie and Dick test described in the Augurt patent, the fabrication of such packs from existing materials and the selection and identification of packs for biological testing result in non-uniformity of tests and involves considerable time and effort. Accordingly, it is desirable to create a disposable, uniform test pack which can replicate the steam penetration qualities of the conventional biological test pack described in the AAMI standard and yet be consistent, small and disposable. However, the conventional test pack required for biological tests is quite different from that used for the Bowie and Dick test. Further, it is desirable in the case of biological testing that the test package be capable of functioning in both a gravity displacement autoclave and in a prevacuum autoclave. These two different autoclave types place different demands on a test package. Specifically, in the prevacuum autoclave, where air is drawn out of the chamber in the first part of the cycle, after which steam under pressure is introduced into the chamber, the vacuum/pressure cycle tends to first deform the package outwardly and then compress the package.

Accordingly, it is an object of the present invention to provide a package adapted to receive a biological test device, which package replicates the functional steam permeability qualities of the standard biological test pack for sterilizer testing. A further object of the invention is to provide a pack that is small and disposable and which provides uniform results from test to test. It is also an object of the invention to provide a test package which can function appropriately in both displacement and prevacuum sterilizers.

In accomplishing these and other objects in accordance with the present invention, applicant's biological test pack comprises an enclosure having within it materials of a desired porosity dimensioned to define an open cavity at its central area. The portion of the porous material immediately surrounding the open cavity is adapted to exhibit a sufficient degree of resilient deformation such that introduction of steam under pressure can deform the package without rupturing it, with the package resuming a desired condition when pressure is equalized throughout the package. In addition, the material of the package is preferably such as to prevent moist steam from dramatically altering the porosity of the porous layer.

In an embodiment of the present invention, multiple layers of semiporous material are spaced apart above and below one another, with multiple layers of highly porous crepe material positioned between them. Alternately, the crepe material may be replaced with a foam. The crepe or foam material is cut to form a cavity in its interior for receiving a biological test device. The sheets of semiporous material immediately above and below the crepe material are preferably of a less dense material than the remainder of the sheets so as to avoid physical injury to the biological test device during the portion of the cycle when steam is introduced under pressure and the package is deformed inwardly. The assembly is inserted in a paper box in which the four lateral sides of the box interior also contain a layer of very low porosity material such as plastic laminated to the box interior.

Further features and advantages of applicant's invention will be apparent from the following detailed description of a presently preferred embodiment of applicant's invention, when taken in conjunction with the appended drawings, wherein.

Figure 2:
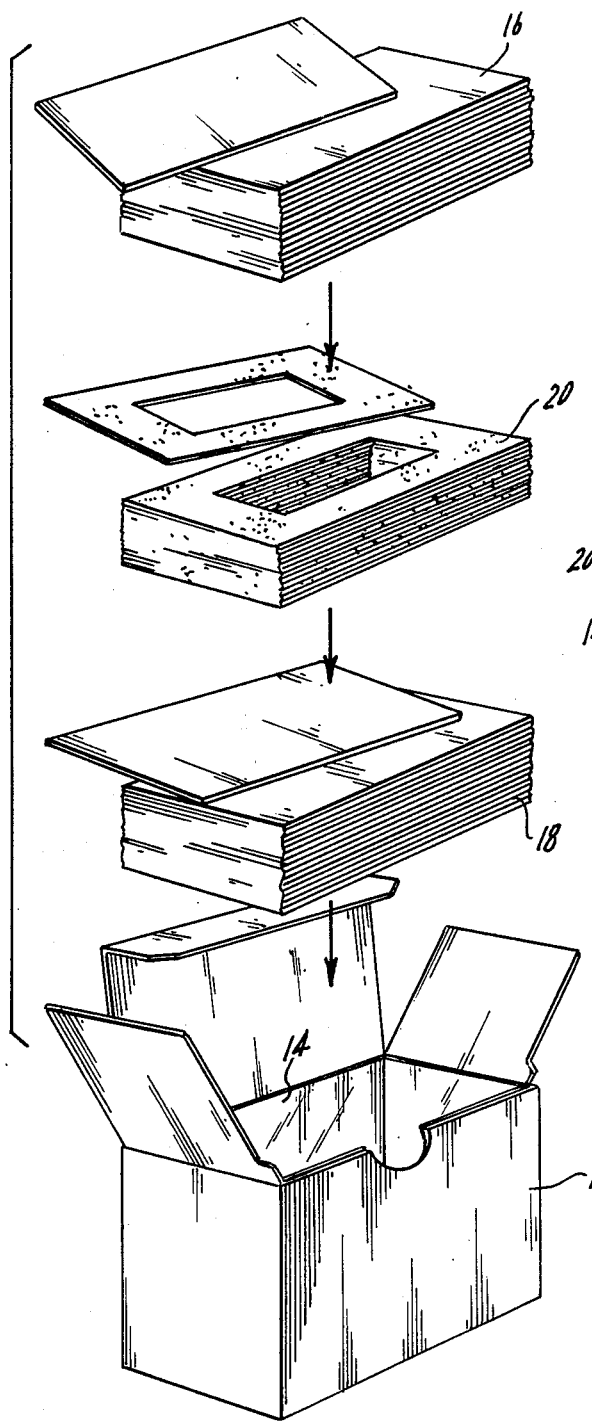
FIG. 2 is an exploded view of applicant's test pack without the biological test device.
Figure 1:
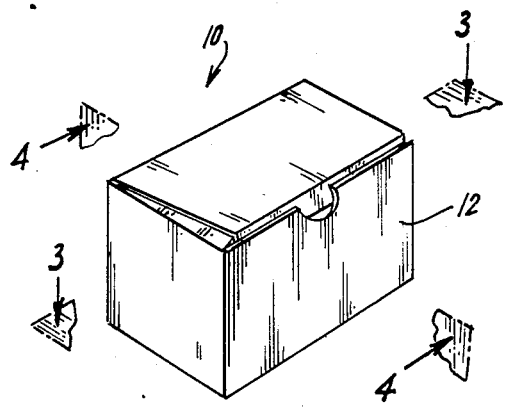
FIG. 1 is a perspective view of applicant's test pack.
Figure 3:
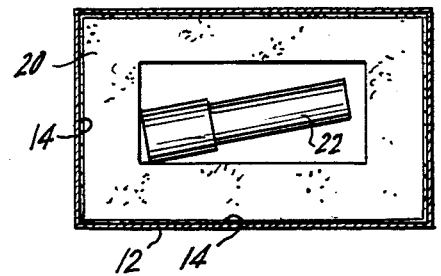
FIG. 3 is a cross-sectional view taken along plane 3 in FIG. 1 with the biological test device in place.
Figure 4:
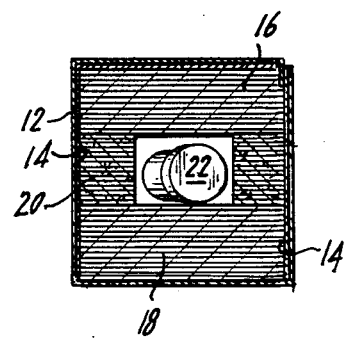
FIG. 4 is a cross-sectional view taken along plane 4 in FIG. 1, with the biological test pack in place.

Referring to the drawings, FIG. 1 shows a biological test pack 10 in its fully assembled and closed condition in accordance with a preferred embodiment of the invention. The pack 10 is comprised of a box 12 which may, for example, have overall dimensions of 4 11/16 inch by 3 1/16 inch by 3 5/16 inch. The box is of bleached sulfate paper and is unvarnished. The interior of the box has a liner 14 glued to to the four lateral sides of the box. The liner is of a relatively impervious material such as 2 mil. polyproplene and renders the four lateral sides of the box relatively immune to the penetration of steam.

The box contains two stacks of semiporous material 16 and 18, separated by a stack of highly porous material 20. Each of the stacks of semiporous material may be formed of filter paper having differing porosities. In a preferred embodiment, each of the stacks (16, 18) are formed with 48 to 52 sheets of filter paper having an approximate basis weight of 214 pounds (per 3,000 square feet) and an approximate thickness of 0.02 inches per sheet. At the interior of these sheets (below the sheets 16 and above the sheets 18) are four sheets of filter paper having an approximate basis weight of 178 pounds (per 3,000 square feet) and an approximate thickness of 0.02 inches per sheet. These interior sheets are less dense than the outer sheets and tend to deform more easily if compression of the package, under pressure of steam, forces them against the biological test device 22.

The porous layer 20 may be composed of approximately 125 sheets of Dexter Steri Wrap (manufactured by C.H. Dexter Division of Dexter Corporation, Windsor Locks, Conn. and sold by Propper Manufacturing Company of Long Island City, N.Y. under the trademark STERI WRAP) with a 3 inch by 1 5/16 inch area cut from the center of each sheet. The height of this central core, when assembled and dry, is approximately 1 inch. This crepe material is treated so that it does not absorb moisture from the steam and maintains its resilience even under the conditions in a prevacuum sterilizer.

The assembled structure is adapted to receive a biological test device 22 which may be of a type well known in the art. An example of this type of test device is the test device described in U.S. Pat. No. 3,661,717.

In practice, applicant's enclosure is opened by opening the box flap, the top stack of semiporous sheets 16 is removed and the biological test device 22 is placed within the cavity formed in layer 20. The top stack 16 is then replaced and the box closed. The box is then placed in the steam autoclave with a normal load and run through a conventional cycle. During this cycle, the rapid evacuation of air from the chamber tends to expand the package, deforming its sides outwardly. Upon the introduction of steam under pressure, the package is relatively quickly deformed from its expanded shape to a compressed state with the sides and particularly the top and bottom of the package deformed inwardly. During this portion of the cycle, the Steri Wrap layers 20 tend to be compressed with the interior layers of the porous paper stacks 16 and 18 approaching or engaging the biological test device 22. However, the crepe material 20 (because of its configuration and the fact that it is designed not to absorb water) remains sufficiently resilient to reassume a relatively uncompressed state subsequent to the initial introduction of steam under pressure. During this physical deformation, the Steri Wrap material also remains porous and continues to function as a simulation of the conventional test pack.

This preferred structure has the further advantage that it functions in a similarly suitable way in a gravity displacement sterilizer. In a displacement sterilizer the temperature of steam is considerably lower than the prevacuumed sterilizer (250° F. as opposed to 272°F.) and the cycle times of such sterilizers are considerably longer (30 minutes for a gravity sterilizer as opposed to approximately 4 minutes for a prevacuume sterilizer). The dynamics for the gravity sterilizer are such that applicant's package is not put through the sharp deformation discussed above. Applicant's package configuration maintains its porosity and steam permeability qualities in either sterilizer type.

Applicant has found that the enclosure formed in accordance with the present invention replicates the steam permeability qualities of the standard biological test pack described in the AAMI standard. Flaws in the sterilization cycle such as inadequate exposure time tend to reduce the penetration of steam to the biological test device 22 within applicant's enclosure. Applicant has found that the test pack described herein adequately replicates the standard test pack so that applicant's test pack reveals a lack of sterility under substantially the same conditions as the standard AAMI test pack. Applicant's pack provides the advantage of being uniform and disposable and avoids many of the problems inherent in the standard test arrangement.

What is claimed is:

1. An enclosure constructed and arranged to receive a biological test device and adapted to be inserted in an autoclave for testing the proper functioning of the autoclave, the enclosure comprising: a first stack of layers of semiporous material; a second stack of layers of semiporous material; said first and second stacks each having selected height and porosity characteristics; said first and second stacks being spaced apart from one another and positioned one above the other; a layer of highly porous material positioned between and in contact with said first and second stacks; said first and second stacks and said layer of highly porous materials forming a disposable pack having top and bottom surfaces formed by the top of one of said first and second stacks and the bottom of the other of said first and second stacks, and side edges formed by the edges of said first and second stacks and the edges of said highly porous layer between said top and bottom surfaces; said highly porous layer having a cavity formed therein for receiving a biological test device; relatively steam impervious material positioned only around the side edges of said pack to inhibit the passage of air and steam through said side edges and neither above said pack top surface nor below said pack bottom surface; and means for retaining said relatively impervious material in position around said side edges.

2. An enclosure in accordance with claim 1 wherein said retaining means is a box and said relatively steam impervious material is secured to said box at the sides thereof which overlay the side edges of the pack.

3. An enclosure in accordance with claim 1 wherein the material of said highly porous layer is sufficiently resilient so that it resumes substantially its original shape after deformation of said pack caused by the introduction of steam under pressure.

4. An enclosure in accordance with claim 1 additionally including a biological test device disposed in said cavity.

5. A method for testing the proper function of an autoclave comprising the steps of: inserting in said autoclave a biological test device encased within a disposable enclosure comprising a first stack of layers of semiporous material, a second stack of layers of semiporous material, said first and second stacks each having selected height and porosity characteristics, said first and second stacks being spaced apart from one another and positioned one above the other, a layer of highly porous material positioned between and in contact with said first and second stacks, said first and second stacks and said layer of highly porous materials forming a disposable pack having top and bottom surfaces formed by the top of one of said first and second stacks and the bottom of the other of said first and second stacks and side edges formed by the edges of said first and second stacks and the edges of said highly porous layer between said top and bottom surfaces, said highly porous layer having a cavity formed therein for receiving a biological test device, a sheet of relatively steam impervious material positioned around the side edges of said pack to inhibit the passage of air and steam through said side edges, and means for retaining said relatively impervious material in position around said side edges; operating said autoclave through its normal sterilization cycle with a normal sterilization load; and, removing the biological test device from said enclosure and determining whether biological material in said test device has been destroyed by sterilization.

6. The method in accordance with claim 5 wherein the relatively steam impervious material is positioned only around the side edges of said pack and neither above the pack top surface nor below the pack bottom surface.

7. The method in accordance with claim 5 wherein the material of said highly porous layer is sufficiently resilient so that it resumes substantially its original shape after deformation of said pack caused by the introduction of steam under pressure.

8. An enclosure constructed and arranged to receive a biological test device and adapted to be inserted in an autoclave for testing the proper functioning of the autoclave, the enclosure comprising: a first stack of layers of semiporous material; a second stack of layers of semiporous material; said first and second stacks each having selected height and porosity characteristics; said first and second stacks being spaced apart from one another and positioned one above the other; a layer of highly porous material positioned between and in contact with said first and second stacks, the material of said highly porous layer being sufficiently resilient so that it resumes substantially its original shape after deformation of said pack caused by the introduction of steam under pressure; said first and second stacks and said layer of highly porous materials forming a disposable pack having top and bottom surfaces formed by the top of one of said first and second stacks and the bottom of the other of said first and second stacks, and side edges formed by the edges of said first and second stacks and the edges of said highly porous layer between said top and bottom surfaces; said highly porous layer having a cavity formed therein for receiving a biological test device; relatively steam impervious material positioned around the side edges of said pack to inhibit the passage of air and steam through said side edges; and means for retaining said relatively impervious material in position around said side edges.

9. An enclosure in accordance with claim 8 wherein said relatively steam impervious material is positioned only around said side edges of said pack and neither above said pack top surface nor below said pack bottom surface.

10. An enclosure in accordance with claim 9 wherein said retaining means is a box and said relatively steam impervious material is secured to said box at the sides thereof which overlay the side edges of the pack.

11. An enclosure in accordance with claim 8 additionally including a biological test device disposed in said cavity.

* * * * *